US007041507B1

(12) United States Patent
Levesque et al.

(10) Patent No.: US 7,041,507 B1
(45) Date of Patent: May 9, 2006

(54) TRANSDIFFENTIATION OF TRANSFECTED EPIDERMAL BASAL CELLS INTO NEURAL PROGENITOR CELLS, NEURONAL CELLS AND/OR GLIAL CELLS

(75) Inventors: Michel F. Levesque, Beverly Hills, CA (US); Toomas Neuman, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/545,428

(22) Filed: Apr. 7, 2000

Related U.S. Application Data

(63) Continuation-in-part of application No. 09/234,332, filed on Jan. 20, 1999, now Pat. No. 6,087,168.

(30) Foreign Application Priority Data

Jan. 20, 2000 (EP) .................................. 00101100
Jan. 20, 2000 (JP) ............................. 2000-048291

(51) Int. Cl.
C12N 15/09 (2006.01)
C12N 15/89 (2006.01)

(52) U.S. Cl. .......................... 435/455; 435/325; 435/6; 435/366; 435/375; 536/23.1; 536/24.5

(58) Field of Classification Search .................... 435/6, 435/7.21, 91.1, 91.31, 91.4, 455, 325, 366, 435/375; 536/23.1, 24.5; 514/44
See application file for complete search history.

(56) References Cited

U.S. PATENT DOCUMENTS

| 5,411,883 | A | 5/1995 | Boss et al. |
| 5,589,376 | A | 12/1996 | Anderson et al. |
| 5,753,506 | A | 5/1998 | Johe |
| 6,087,168 | A | 7/2000 | Levesque et al. |

FOREIGN PATENT DOCUMENTS

WO   WO 97/11095   3/1997

OTHER PUBLICATIONS

Branch, TIBS 23, pp. 45-50, Feb. 1998.*
Flanagan et al., Nature Biotech 17: 48-52, Jan. 1999.*
Gilbert, Scott F., Developmental Biology, Fifth Edition, Sinauer Associates, Inc. Publishers, Sunderland, Mass., 1997, pp. 297-299.*
Matsas, R. and Tsacopoulos, M., Eds., The Functional Roles of Glial Cells in Health and Disease, Dialogue between Glia and Neurons, Kluwer Academic Pblishers, New York, NY, 1999, pp. v-vi and 3-12.*
Svendsen et al. Neurons from stem cells:preventing an identity crisis. Nature Reviews, vol. 2, Nov. 2001, pp. 831-834.*
Smith et al. Journal of Dematological Science. vol. 18, 1998, pp. 19-29.*
Kutzner et al. Cutaneous Myoepithelioma. The American Journal of Surgical Pathology. vol. 25, No. 3, 2001, pp. 348-355.*
Hakelien et al. Novel Approaches to Transdifferentiation. Cloning and Stem Cells, vol. 4, No. 4, 2002, pp. 379-387.*
Wickelgren, Ingrid, *Teaching the Spinal Cord to Walk*, Science, vol. 279, pp. 319-321 (Jan. 16, 1998).
Zhu, G., et al., *Sonic hedgehog and BMP2 exert opposing actions on proliferation and differentiation of embryonic neural progenitor cells*, Dev. Biol., 215(1):118-29 (Nov. 1999) Abstract Only.
Zuniga, A., et al., *Signal relay by BMP antagonism controls the SHH/FGF4 feedback loop in vertebrate limb buds*, Nature, 401(6753):598-602 (Oct. 1999) Abstract Only.
Bellefroid, Eric J. et al., *X-MyT1, a Xenopus C2HC-Type Zinc Finger Protein with a Regulatory Function in Neuronal Differentiation*, Cell, vol. 87, 1191-1202, Dec. 1996.
Guillemot, F., et al., *Dynamic expression of the murine Achaete-Scute homologue Mash-1 in the developing nervous system*, Mech. Dev., 42(3):171-85 (Aug. 1993) Abstract Only.
Hirota Y., et al., *Musashi and seven in absentia downregulate tramtrack through distinct mechanisms in drosophila eye development*, Mech. Dev., 87(1-2):93-101 (Sep. 1999) Abstract Only.
Ishibashi, M., et al., *Targeted disruption of mammalian hairy and Enhancer of split homolog-1 (HES-1) leads to upregulation of neural helix-loop-helix factors, premature neurogenesis, and severe neural tube defects*, Genes & Development, 9:3136-3148 (1995).
Ishibashi, M., et al., *Persistent expression of helix-loop-helix factor factor HES-1 prevents mammalian neural differentiation in the central nervous system*, The EMBO Journal, vol. 13, No. 8, pp. 1799-1805 (1994).
Lee, Jacqueline E., et al., *Conversion of Xenopus ectoderm into Neurons by NeuroD, a Basic Helix-Loop-Helix Protein*, Science, vol. 268, pp. 836-844 (May 1995).
Lein, P., et al., *Osteogenic protein-1 induces dentritic growth in rat sympathetic neurons*, Neuron, 15(3):597-605 (Sep. 1995) Abstract Only.

(Continued)

Primary Examiner—Sean McGarry
(74) Attorney, Agent, or Firm—Jones Day

(57) ABSTRACT

Disclosed is an in vitro method of transdifferentiating an epidermal basal cell into a cell having one or more morphological, physiological and/or immunological features of a glial cell. Also disclosed are such transdifferentiated cells and cell cultures derived from them. A kit for converting, in vitro, epidermal basal cells into cells having one or more morphological, physiological and/or immunological features of a glial cell is also disclosed.

18 Claims, 2 Drawing Sheets

OTHER PUBLICATIONS

Ma, Qiufu, et al., *Identification of neurogenin, a Vertebrate Neuronal Determination Gene*, Cell, vol. 87, 43-52 (Oct. 4, 1996).

Mayer-Proschel, M., et al., *Isolation of lineage-restricted neuronal precursors from multipotent neuroepithelial stem cells*, Neuron, 19(4):773-85 (Oct. 1997) Abstract Only.

McCormick, Mary B., et al., *neuroD2 and neuroD3: Distinct Expression Patterns and Transcriptional Activation Potentials within the neuroD Gene Family*, Molecular and Cellular Biology, vol. 16, No. 10, p. 5792-5800 (Oct. 1996).

Nagata, T., et al., *Structure, backbone dynamics and interactions with RNA of the C-terminal RNA-binding domain of a mouse neural RNA-binding protein, Musashi 1*, J. Mol. Biol., 287(2):315-30 (Mar. 1999) Abstract Only.

Nakata, Katsunori, et al., *Xenopus Zic3, a primary regulator both in neural and neural crest development*, Proc. Natl. Acad. Sci. USA, vol. 94, pp. 11980-11985 (Oct. 1997).

Park, J.K., et al., *Bipotent cortical progenitor cells process conflicting cues for neurons and glia in a hierarchical manner*, J. Neurosci, 19(23):10383-9 (Dec. 1999) Abstract Only.

Pera, E. et al., *Ectodermal patterning in the avian embryo: epidermis versus neural plate*, Development, 126(1):63-73 (Jan. 1999) Abstract Only.

Rayl, A.J.S., *Transplanted Neurons Migrate Widely in the Adult Brain*, The Scientist, vol. 13, #18, p. 33 (Sep. 13, 1999).

Renoncourt, Y., et al., *Neurons derived in vitro from ES cells express homeoproteins characteristic of motoneutrons and interneutrons*, Mech. Dev., 79(1-2):185-97 (Dec. 1998) Abstract Only.

Sang, Q., et al., *Innervation of the esophagus in mice that lack MASH1*, J. Comp. Neurol, 408(1):1-10 (May 1999) Abstract Only.

Sasai, Y., *Identifying the missing links: genes that connect neural induction and primary neurogenesis in vertebrate embyros*, Neuron, vol. 21, No. 3, pp. 455-458 (Sep. 1998).

Stemple, D.L., et al., *Neural stem cells are blasting off*, Neuron, vol. 16, No. 1, pp. 1-4 (Jan. 1997).

Suzuki, Atsushi, et al., *Xenopus msx1 mediates epidermal induction and neural inhibition by BMP4*, Development, vol. 124, pp. 3037-3044 (1997).

Tanabe. Yasuto, et al., *Diversity and Pattern in the Developing Spinal Cord*, Science, vol. 274, pp. 1115-1123, (Nov. 15, 1996).

Wichterle, H., et al., *Young neurons from medial ganglionic eminence disperse in adult and embryonic brain*, Nat Neurosci, 2(5):461-6 (May 1999) Abstract Only.

Wichterle, H., et al., *Direct evidence for homotypic, glia-independent neuronal migration*, Neuron, 18(5):779-91 (May 1997) Abstract Only.

Honoré, Eric, et al., *L'induction neurale chez les vertébrés: le cerveau par défaut*, Médecine/Science, vol. 13, No. 2, pp. 192-200 (Feb. 1997) (English summary attached).

Nagai, Takeharu, et al., *The Expression of the Mouse Zic1, Zic2, and Zic3 Gene Suggests an Essential Role for Zic Genes in Body Pattern Formation*, Developmental Biology, vol. 182, pp. 299-313 (1997). Article No. DB968449.

Kim, Peter et al., *XATH-1, A Vertebrate Homolog of Drosophila atonal, Induces Neuronal Differentiation within Ectodermal Progenitors*, Developmental Biology, vol. 187, pp. 1-12 (1997). Article No. DB978572.

Streit, Andrea et al., *Neural Induction, a bird's eye view*, TIG, vol. 15, No. 1, pp. 20-24 (Jan. 1999).

* cited by examiner

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens
<220> FEATURE:
<221> NAME/KEY: gene
<222> LOCATION: (0)...(0)
<223> OTHER INFORMATION: MSX1 antisense oligonucleotide sequence MSX1-1

<400> SEQUENCE: 1
gacaccgagt ggcaaagaag tcatgtc                                         27

<210> SEQ ID NO 2
<211> LENGTH: 24
<212> TYPE: DNA
<213> ORGANISM: Homo sapiens
<220> FEATURE:
<221> NAME/KEY: gene
<222> LOCATION: (0)...(0)
<223> OTHER INFORMATION: MSX1 antisense oligonucleotide sequence MSX1-1

<400> SEQUENCE: 2
```

```
                                   -continued cggcttcctg tggtcggcca tgag                                          24

<210> SEQ ID NO 3
<211> LENGTH: 35
<212> TYPE: DNA
<213> ORGANISM: Homo sapiens
<220> FEATURE:
<221> NAME/KEY: gene
<222> LOCATION: (0)...(0)
<223> OTHER INFORMATION: HES1 open reading frame 5' sequence (HES1-1)

<400> SEQUENCE: 3
accggggacg aggaattttt ctccattata tcagc                              35

<210> SEQ ID NO 4
<211> LENGTH: 40
<212> TYPE: DNA
<213> ORGANISM: Homo sapiens
<220> FEATURE:
<221> NAME/KEY: gene
<222> LOCATION: (0)...(0)
<223> OTHER INFORMATION: HES1 open reading frame 5' sequence (HES1-2)

<400> SEQUENCE: 4
cacggaggtg ccgctgttgc tgggctggtg tggtgtagac                         40
```

TRANSDIFFENTIATION OF TRANSFECTED EPIDERMAL BASAL CELLS INTO NEURAL PROGENITOR CELLS, NEURONAL CELLS AND/OR GLIAL CELLS

This application is a continuation-in-part of U.S. patent application Ser. No. 09/234,332, filed on Jan. 20, 1999, which issued as U.S. Pat. No. 6,087,168, on Jul. 11, 2000, and also claims priority from European Patent Application Serial No. 00101100.6, filed on Jan. 20, 2000, and Japanese Application Patent Application No. 2000-048291, filed Jan. 20, 2000.

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. Field of the Invention

The present invention is related to the medical arts, particularly to the field of neural tissue regeneration.

2. Discussion of the Related Art

The human nervous system comprises highly diverse cell types that make specific interconnections with one another. The nervous system includes the peripheral nerves and the central nervous system. The central nervous system includes the brain, cranial nerves, and spinal cord. Once damaged, the central nervous system of the adult has limited potential for structural self-repair. The general inability of the adult to generate new neurons (excitable cells specialized for the transmission of electrical signals from one part of the body to another) typically prevents the regeneration of neural tissues. This limitation has hindered the development of therapies for neurological injury, for example from stroke or physical trauma, or for degenerative diseases, such as Huntington disease, Alzheimer disease, and Parkinsonism. The moderate success of fetal tissue transplantation therapy for Parkinsonism suggest that cell replacement therapy can be a valuable treatment for neurological injury and degeneration.

Thus, there is a long felt need in the biomedical field for a method of generating neurons for use in the treatment of various neurological traumas, diseases, disorders, or maladies via the direct transfer of neuronal cells in a cell replacement therapy approach.

A gene therapy approach, on the other hand, is required to treat other types of nervous system disorders. Because the brain is protected by a blood-brain barrier that effectively blocks the flow of large molecules into the brain, peripheral injection of growth factor drugs, or other potentially therapeutic gene products, is ineffective. Thus, a major challenge facing the biotechnology industry is to find an efficient mechanism for delivering gene therapy products, directly to the brain, so as to treat neurological disorders on the molecular level. In this regard, a renewable source of human neural cells could serve as a vehicle to deliver gene therapy products to the brain and the rest of the central nervous system.

Until recently, the only source of donor material for these promising therapies was fetal tissue. However, the use of fetal tissue presents significant ethical and technical problems, including the limited availability of fetal tissue, the possible immuno-rejection of donor material by the recipient, and the risk of disease transmission by donor material.

Several attempts have been made to address the shortage of donor material by culturing neural progenitor cells, or neural stem cells. For example, Boss et. al taught a method for isolation and proliferation of neural progenitor cells directed to growth, storage, production and implantation of the proliferated donor cells. (Boss et. al, Proliferated Neuron Progenitor Cell Product and Process, U.S. Pat. No. 5,411,883). Anderson et. al taught a method for isolation and clonal propagation of donor mammalian neural crest stem cells capable of self renewal and differentiation into neural or glial cells. (Anderson et. al, Mammalian Neural Crest Stem Cells, U.S. Pat. No. 5,589,376). Johe taught a method for isolation, propagation and directed differentiation of stem cells from the central nervous system of embryonic and adult mammalian donors. (Johe, Isolation Propagation and Directed Differentiation of Stem Cells from Embryonic and Adult Central Nervous System of Mammals, U.S. Pat. No. 5,753,506).

Neural progenitor cells normally develop from embryonic ectodermal tissue. Bone Morphogenetic Protein (BMP) is a family of repressors that prevents ectoderm from developing into its default state of neural tissue and induces the development instead of epidermal tissue. (Y. Tanabe & T. M. Jessell, *Diversity and Pattern in the Developing Spinal Cord*, Science 274:1115 [1996]; Y. Sasai, *Identifying the missing links: genes that connect neuronal induction and primary neurogenesis in vertebrate embryos*, Neuron 21:455–58 [1998]; Y. Furuta et al, *Bone morphogenetic proteins (BMPs) as regulators of dorsal forebrain development*, Development 124(11):2203–2212 [1997]). BMP 2 and BMP 4 induce epidermal differentiation. (E. Pera et al., *Ectodermal Patterning in the Avian Embryo: Epidermis Versus Neural Plate*, Development 126:63 [1999]).

BMP's can also induce cartilage formation. Hattersley et al. showed that adding BMP 13 to a cell line derived from mouse limb buds leads to the formation of chondroblast-like cells and taught a method for using BMP 13 to induce articular cartilage formation at the site of congenital or trauma induced damage and for using BMP 9 to maintain cartilage. (Hattersley et al., Cartilage Induction by Bone Morphogenetic Proteins, U.S. Pat. No. 5,902,785).

BMP signal transduction appears to be mediated by msx1, which is an immediate early response gene involved in epidermal induction and inhibition of neuronal differentiation. When Suzuki et al. injected BMP RNA into *Xenopus* embryos, they detected msx1 RNA production; when they injected msx1 RNA, the embryos lost neuronal structures such as eyes. (Suzuki et al., *Xenopus msx1 Mediates Epidermal Induction and Neural Inhibition by BMP4*, Development 124:3037 [1997]). When msx1 was added directly to dissociated ectodermal cells, epidermal development was up-regulated and neural development was down-regulated. Similarly in humans, BMP growth factors induce expression of the homeodomain transcription factor MSX1 in ectodermal cells. Once MSX1 is expressed, induction of the neuronal determination genes is simultaneously suppressed and neuronal differentiation is inhibited.

BMP seems to down-regulate neural development through at least two mechanisms: proteolysis of MASH1 protein and inhibition of Zic3 production. Exposure of neural progenitor cells to BMP triggered a rapid loss of MASH1 protein, a transcription factor that is homologous to the *Drosophila* Achaete-Scute Complex (ASH1) and required for the production of olfactory receptor neurons. (Shou et al., *BMPs Inhibit Neurogenesis by a Mechanism Involving Degradation of a Transcription Factor*, Nat. Neurosci. 2: 339 [1999]). Micro-injection of the dominant negative form of the BMP receptor, an inhibitor of BMP, into *Xenopus* embryos induced production of Zic3, a protein that augments neural development. (Nakata et al., *Xenopus Zic3, a Primary Regulator Both in Neural and Neural Crest Development*, Proc. Natl. Acad. Sci. 94: 11980 [1997]).

Antagonists of BMP signal transduction activity include fetuin glycoprotein, also known as α2-HS glycoprotein in humans, and the DAN family of BMP antagonists, such as noggin, chordin, follistatin, and gremlin. (R. Merino et al., *The BMP antagonist Gremlin regulates outgrowth, chondrogenesis and programmed cell death in the developing limb*, Development 126(23):5515–22 [1999]; D. Sela-Donnenfeld and C. Kalcheim, *Regulation of the onset of neural crest migration by coordinated activity of BMP4 and noggin in the dorsal neural tube*, Development 126(21):4749–62 [1999]). For example, Demetriou et al. showed that fetuin blocks osteogenesis, a function promoted by BMP, in a culture of rat bone marrow cells and that a fetuin derived peptide binds BMP 2. (M. Demetriou et al., *Fetuin/Alpha2-HS Glycoprotein is a Transforming Growth Factor-Beta Type II Receptor Mimic and Cytokine Antagonist*, J. Biol. Chem. 271:12755–61 [1996]). During embryonic and early postnatal development, Fetuin was shown to be present in a sub-population of cells in the retinal ganglion cell layer, the neuroblastic layer, and portions of the developing cerebellum. (Kitchener et al., *Fetuin in Neurons of the Retina and Cerebellum During Fetal and Postnatal Development of the Rat*, Int. J. Dev. Neurosci. 17: 21 [1999]).

Fetuin has been used as an additive in serum free media. Ham et al. taught the use of fetuin as an additive in serum free media for the growth of normal human muscle satellite cells directed at transplantation to the muscles of patients afflicted with muscle degenerative diseases. (Ham et al., Media for Normal Human Muscle Satellite Cells, U.S. Pat. No. 5,143,842; Ham et al., Media for Normal Human Muscle Satellite Cells, U.S. Pat. No. 5,324,656). Baker taught the use of fetuin as an additive in a defined serum free media that is capable of growing a wide range of cell suspensions and monolayers. (Baker, Serum-Free Cell Culture Medium and Process for Making Same, U.S. Pat. No. 4,560,655).

Other factors beside BMP appear to be involved in regulating neural differentiation. Ishibashi et al. demonstrated that persistent expression of Hairy and Enhancer of Split Homolog-1 (HES1) severely perturbs neuronal and glial differentiation. They infected the lateral ventricles of the brains of embryonic mice with a retrovirus that produced HES1. This led to failed migration and differentiation in the developing cells that were infected. (Ishibashi et al., *Persistent Expression of Helix-Loop-Helix Factor HES-1 Prevents Mammalian Neural Differentiation in the Central Nervous System*, The EMBO Journal 13: 1799 [1994]). Ishibashi et al. also disrupted the HES1 gene in mice and observed earlier than usual neurogenesis. They concluded that HES1 controls the timing of neurogenesis. (Ishibashi et al., *Targeted Disruption of Mammalian Hairy and Enhancer of Split Homolog-1 (HES-1) Leads to Up-Regulation of Neural Helix-Loop-Helix Factors, Premature Neurogenesis, and Severe Neural Tube Defects*, Genes &Development 9: 3136 [995]). In addition retinoids, such as retinoic acid, may play a role in inducing the differentiation of some neural cell populations. (e.g., Y. Renoncourt et al., *Neurons derived in vitro from ES cells express homeoproteins characteristic of motoneurons and interneurons*, Mechanisms of Development 79:185–97 [1998]).

Thus, the differentiation of neuronal tissue involves the interaction of numerous positive and negative regulatory molecules, In response to developmental signals within each cell and its surrounding microenvironment, every neuronal population expresses a specific set of neural markers, neurotransmitters, and receptors. As neural progenitor cells differentiate into other neuronal cell types in response to physiological signals in the microenvironment, the set that is expressed will be different. (E.g., see D. L. Stemple and N. K. Mahanthappa, *Neural stem cells are blasting off*, Neuron 18:1–4 [1997]; Y. Renoncourt et al., *Neurons derived in vitro from ES cells express homeoproteins characteristic of motoneurons and interneurons*, Mechanisms of Development 79:185–97 [1998]; A. J. Kalyani et al., *Spinal cord neuronal precursors generate multiple neuronal phenotypes in culture*, J. Neurosci. 18(19):7856–68 [1998]). Each neuronal cell type is characterized by several criteria including morphology (e.g., long processes or neurites), expression of a set of neural-specific markers (e.g., neurofilament M, neural-specific tubulin, neural-specific enolase, microtubule associated protein 2, and others), synthesis of neurotransmitters (e.g., dopamine or expression of tyrosine hydroxylase, the key enzyme in dopamine synthesis), and membrane excitability.

One of the central principles of modern neurobiology is that after differentiation each of the major projection neurons, if not all neuronal cell types, requires for its survival specific cytokines, i.e., neurotrophic or nerve growth factors, to reach their target neuronal cells. Neuropathies in many diseases may be caused by, or involve lack of, such nerve growth factors. These nerve growth factors represent the next generation of preventative and therapeutic drugs for nervous system disorders. Most of the growth factors known so far in the nervous system were discovered by their effects on peripheral nerves and these most likely represent a very minor fraction of existing growth factors in the brain. Search for growth factors from the brain has been difficult mainly because particular neuronal cell types are difficult to isolate from the brain and maintain in defined culture conditions.

Due to this limitation, drug discovery by traditional pharmacology directed to the central nervous system has been performed using whole brain homogenate and animals. These studies mostly produced analogs of neurotransmitters with broad actions and side effects. But as more and more neurotransmitter receptors and signal transducing proteins have been identified from the brain, it is becoming clear that the dogma of one neurotransmitter activating one receptor is an over-simplification. Most receptor complexes in neurons are composed of protein subunits encoded by several genes and each gene synthesizes many different variations of the protein. These variations result in a wide range of possible receptor combinations, and not a single receptor that can interact with a neurotransmitter. Consequently, a range of signal output may be produced by a single neurotransmitter action. The specific signal effected by a neurotransmitter on a neuron, then, depends on which receptor complex is produced by the cell. Thus, cellular diversity must parallel the molecular diversity and constitute a major structural element underlying the complexity of brain function, and a source of diverse neuronal cell types that can be cultured for drug screening purposes is needed.

Therefore, there remains a need in the field of neurological research and applied neurobiology for a renewable non-fetal source of neural progenitor cells and cells having characteristics specifically associated with neuronal or glial cell types, for use in research, cell therapy, or gene therapy. Importantly, the use of such cells could eliminate a need for fetal human tissue in therapeutic approaches aimed at restoring neurological function by intracerebral transplantation of nervous system cells. These and other benefits the present invention provides as described herein.

SUMMARY OF THE INVENTION

The present invention relates to a method of transdifferentiating an epidermal basal cell into a cell having one or more morphological, physiological and/or immunological feature(s) of a neural progenitor cell, a neuronal cell, or a glial cell. The method involves culturing a proliferating epidermal basal cell population comprising one or more epidermal basal cell(s) derived from the skin of a mammalian subject. These epidermal basal cell(s) are transfected, in vitro, with one or more eukaryotic expression vector(s) that contain at least one cDNA encoding a human neurogenic transcription factor, or homologous non-human counterpart, or active fragment(s) thereof, such as NeuroD1, NeuroD2, ASH 1, Zic1, Zic3, or MyT1, such that at least one of the neurogenic transcription factor(s) is expressed in the cell. The transfected cell(s) are grown in an in vitro growth medium in which is present at least one antisense oligonucleotide comprising a segment of a human MSX1 gene and/or human HES1 gene, or homologous non-human counterpart of either of these, thereby suppressing at least one negative regulator of neuronal differentiation; and the cell(s) are, optionally, further grown with a retinoid and at least one neurotrophin, such as BDNF, CNTF, PDGF, NGF, NT-3, NT-4, or sonic hedgehog, or a cytokine comprising IL-6. By the inventive method the cell(s) is transdifferentiated into a cell having one or more morphological, physiological and/or immunological feature(s) of a neural progenitor, neuronal, or glial cell.

The present invention also relates to a transdifferentiated cell(s) of epidermal origin. The inventive transdifferentiated cell is a cell of epidermal basal cell origin that displays one or more morphological, physiological and/or immunological feature(s) of a neural progenitor, neuronal, or glial cell. The physiological and/or immunological feature can be, but is not limited to, expression of one or more marker(s) specific to a neural progenitor, neuronal, or glial cell, by which the transdifferentiated cell is recognized as a neural progenitor, neuronal or neuron-like cell, or a glial or glial-like cell.

The present invention also relates to cell cultures derived from the inventive transdifferentiated cell(s).

The present invention is also directed to a method of delivering locally secretable regulatory factors using the inventive transdifferentiated cells, which are genetically modified, before or after their transdifferentiation, with an expression vector comprising a DNA encoding a preselected secretable regulatory factor or a biochemical precursor thereof, or a DNA encoding an enzyme that catalyzes the synthesis of either of these. The genetically modified, transdifferentiated cells are implanted into a mammalian subject, and the implanted cells secrete the locally secretable regulatory factor.

The present invention also relates to method of using the inventive transdifferentiated cell(s) to identify a novel nerve growth factor or potential chemotherapeutic agent. The methods involve transdifferentiating a population of proliferating epidermal basal cells into neuronal progenitor cells, neuronal cells, or glial cells; culturing the transdifferentiated cells; exposing the cultured cells, in vitro, to a potential nerve growth factor (i.e., neurotrophin or neurotrophic factor) and/or potential chemotherapeutic agent; and detecting the presence or absence of an effect of the potential nerve growth factor and/or potential chemotherapeutic agent on the survival of the cells or on a morphological or electrophysiological characteristic and/or molecular biological property of the cells. The presence of an effect altering cell survival, a morphological or electrophysiological characteristic and/or a molecular biological property of the cells indicates the activity of the potential nerve growth factor and/or potential chemotherapeutic agent.

The present invention also relates to a method of using the inventive transdifferentiated cell(s) to screen a potential chemotherapeutic agent to treat a nervous system disorder of genetic origin. In the method the epidermal basal cells are derived from a human subject having a particular nervous system disorder of genetic origin. The cells are transdiffentiated in accordance with the inventive method. The transdifferentiated cells are cultured and exposed, in vitro, to a potential chemotherapeutic agent. The method involves detecting the presence or absence of an effect of the potential chemotherapeutic agent on the survival of the cells or on a morphological or electrophysiological characteristic and/or molecular biological property of said cells. An effect altering cell survival, a morphological or electrophysiological characteristic and/or a molecular biological property of the cells indicates the activity of the chemotherapeutic agent.

The present invention is also related to a kit for transdifferentiating an epidermal basal cell into a cell having one or more morphological, physiological and/or immunological feature(s) of a neural progenitor, neuronal, or glial cell. The kit is useful for practicing the inventive methods.

The present invention is directed to methods of converting, or transdifferentiating, epidermal cells into different types of neural cells having numerous uses in the field of applied neurobiology. In particular, the newly created neurons of the invention can be used in both cell therapies and gene therapies aimed at alleviating neurological disorders and diseases. Further, the invention obviates the need for human fetal tissue as a renewable source of neurons to be used in various medical and research applications.

These and other advantages and features of the present invention will be described more fully in a detailed description of the preferred embodiments which follows.

DETAILED DESCRIPTION OF THE PREFERRED EMBODIMENTS OF THE INVENTION

Figure 1A:
FIG. 1. Transdifferentiation of epidermal basal cells into neuronal cells. Dedifferentiated epidermal basal cells were transfected with NeuroD1+Zic1+MyT1 and simultaneously treated with antisense oligonucleotides corresponding to a portion of MSX1 and HES transcription factors. (A) epidermal basal cells, (B) dedifferentiated epidermal basal cells, (C) newly created neurons, 25% of cells are Neurofilament M immunoreactive 5 days after transfection and treatment with BDNF and all-trans retinoic acid.
Figure 1B:
Figure 1C:

An awareness of the difficulties currently associated with neuronal cell or gene therapy approaches, as these pertain to the use of alternative sources of neuronal cells, especially those used for autologous transplantation, has led to the present invention. The present invention provides methods to convert, or transdifferentiate, epidermal cells into different types of neuronal cells that can be used for intracerebral transplantation. Importantly, the present invention also allows for genetic manipulation of the newly created neurons.

A significant aspect of the present invention is that it permits the use of a patient's own cells to develop different types of neuronal cells that can be transplanted after in vitro growth and transdifferentiation. Thus, this technology eliminates the problems associated with transplantation of non-host cells, such as, immunological rejection and the risk of transmitting disease.

The present invention can be used to generate neurons from an individual patient, thus making autologous transplantations possible as a treatment modality for many neurological conditions including neurotrauma, stroke, neurodegenerative diseases such as Parkinson's disease, Huntington disease, Alzheimer's diseases. Thus, the invention provides for neurological therapies to treat the disease or trauma of interest.

To summarize, this technology provides a plentiful source of neurons for clinical treatments which require transplantation of neurons 1) to compensate for a loss of host neurons, or 2) as vehicles to deliver genetically-based drugs. Further, the invention provides a novel neurological tool for use in basic research and drug screening.

The theoretical molecular basis of the present invention exploits the orchestrated actions in neuronal development of numerous molecular processes including epigenetic signaling and activation of specific transcription factor systems. During development, ectodermal cells develop into neuronal tissue or epidermis, depending on the signals they receive from the surrounding cells. At this early developmental stage, activation of various members of the bone morphogenetic protein family (BMP) of growth factors results in epidermal differentiation, while blocking their action results in neuronal differentiation. (See Tanabe and Jessel, 1996, for a review.) This differentiation pathway is due to the action of BMP growth factors which induce expression of the homeodomain transcription factor MSX1 in ectodermal cells. Once MSX1 is expressed, induction of the neuronal determination genes is simultaneously suppressed and neuronal differentiation is inhibited. (Suzuki et al., 1997).

Alternatively, retinoic acid and Sonic Hedgehog (Shh) signaling are responsible for the induction of expression of several neuronal determination and differentiation genes whose activity is essential for neuronal differentiation. (See Tanabe and Jessel, 1996, for a review.) In particular, data demonstrate that over-expression of several neurogenic basic Helix-Loop-Helix (bHLH) and Zinc-finger transcription factors results in conversion of non-determined ectoderm into neuronal tissue. Additionally, forced expression of bHLH transcription factors, NeuroD1, NeuroD2 (Lee, J. E. et al., *Conversion of Xenopus ectoderm into neurons by neuroD, a basic helix-loop-helix protein*, Science 268, 836–844 [1995]; McCormick, M. B. et al., *NeuroD2 and NeuroD3: distinct expression patterns and transcriptional activation potentials within the neuroD gene family*, Mol. Cell. Biol. 16, 5792–5800 [1996]), or neurogenin 1 (Ma, Q. et al., *Identification of neurogenein, a vertebrate neuronal determination gene*, Cell 87, 43–52 [1996]), or Zinc-finger transcription factors MyT1 (Bellefroid, E. J. et al., *X-MyT1, a Xenopus C2HC type zinc finger protein with a regulatory function in neuronal differentiation*, Cell 87, 1191–1202 [1996]) or Zic3 (Nakata et al., [1997]), results in induction of additional neurogenic transcription factors and initiation of neuronal differentiation of amphibian ectodermal cells.

Moreover, at the level of gene regulation, the effect of neurogenic bHLH transcription factors is antagonized by the HES family of transcription factors which are known to suppress transcription. Over-expression of HES1 protein in developing neuronal cells blocks neuronal differentiation (Ishibashi et al., 1994), whereas blocking its expression stimulates neuronal differentiation (Ishibashi et al., 1995). Thus, neuronal differentiation, like other biological process, is regulated by both positive and negative factors.

The molecular regulatory mechanisms known to be operational during amphibian development were used as the theoretical basis for the present invention. The methods and cell products of the invention are based on the discovery that induced expression of a transcription factor that positively regulates human neuronal differentiation, performed in concert with the suppression of a negative regulator of human neuronal differentiation, results in the conversion of epidermal cells into newly created neurons.

The inventive method, which exploits these molecular mechanisms, results in epidermal basal cells being transdifferentiated into cells having one or more morphological, physiological and/or immunological features of a neural progenitor, neuronal or glial cell. Morphological features include, for example, neurite-like process(es) at least about 50 micrometers in length, characteristic of neuronal cells. Physiological and/or immunological features include expression of one or more specific markers and/or characteristic physiological responses to neural growth factors and other cytokines. Electrochemical characteristics of the cells, or particularly the cell membranes, are also included among physiological features, as are production and secretion by the transdifferentiated cells of regulatory factors such as dopamine or γ-aminobutyric acid (GABA), characteristic of various neuronal cell types.

In accordance with the inventive method, a proliferating epidermal basal cell population is cultured. Thus, the method of transdifferentiating or converting epidermal basal cells into newly created neural progenitors, neurons, and glial cells begins with obtaining epidermal cells from a mammalian subject's (e.g., a human patient's) skin. The cells of the proliferating epidermal basal cell population are derived from any mammalian subject, including a human subject. The cell(s) can be derived directly from a tissue sample resulting from a surgical procedure such as a skin biopsy of the subject, or can be derived indirectly from cultured or stored epidermal basal cells of the subject.

Epidermal basal cells in a skin tissue sample or in a cultured mixed population of basal and keratinized non-basal epidermal cells, are preferably separated from the terminally differentiated keratinized epidermal cells by exposing the mixed cell population to a calcium-free growth medium. For purposes of the present invention, a calcium-free medium contains less than $10^{-6}$ M calcium cations ($Ca^{2+}$). Low calcium cation concentration results in the stripping of the keratin-forming upper epidermal layers from the basal cells. (E.g., P. K. Jensen and L. Bolund, *Low $Ca_{2+}$ stripping of differentiating cell layers in human epidermal cultures: an in vitro model of epidermal regeneration*, Experimental Cell Research 175:63–73 [1988]). The basal cells are then physically separated, selected or isolated from the keratinized cells by any convenient method, such as aspiration or decantation. Calcium cations are required to support development of keratinocytes (skin cells) from basal cells, and returning calcium to the growth medium results in rapid basal cell proliferation in the dedifferentiated cell population (Jensen and Bolund [1988]), and, thus, a proliferating epidermal basal cell population is cultured. Beyond this, it is not necessary to do a dedifferentiating step with respect to individual epidermal basal cell(s) after they are separated, isolated, or selected from the differentiated keratinized cells.

In proliferating cell types other than epidermal basal cell, however, calcium may not be necessary to support development of any particular developmental pathway that is being deregulated. Other means to achieve the desired end of dedifferentiation involve treating the cells with specific growth factor or cytokines. Also, altering the specific gene expression pathway that is responsible for differentiation of epidermal cells by genetic manipulation may be used instead of eliminating calcium in the growth media. Moreover, elimination of calcium may not be required if other than proliferating epidermal basal cells are used.

Transfecting or otherwise genetically modifying the epidermal basal cells is then done in vitro with one or more expression vector(s) containing at least one cDNA encoding a neurogenic transcription factor responsible for neural differentiation. Suitable cDNAs include the basic-helix-loop-helix activators, such as NeuroD1, NeuroD2, ASH1, and zinc-finger type activators, such as Zic3, and MyT1, or other cDNAs including bHLH and/or Zn-finger neurogenic genes. The transcription factors are preferably of human origin, but homologous, non-human counterparts can also be utilized in the invention. Sequences of such non-human counterparts of NeuroD1, NeuroD2, ASH1, Zic1, Zic3, and MyT1 are available from, for example, the GenBank database of NCBI (www.ncbi.nlm.nih.gov). The neurogenic transcription factor gene(s) is operatively linked to a promoter of the expression vector, i.e., a transcriptional unit is formed from which the gene is transcribed, producing mRNA from which gene product is translated in the cell after gene delivery. Therefore, in accordance with the inventive method, expression of the neurogenic transcription factor(s) is preferably controlled by a constitutively expressed eukaryotic promoter, such as a cytomegalovirus (CMV) promoter.

Gene delivery to the cell is by any suitable in vitro gene delivery method. (E.g., D. T. Curiel et al., U.S. Pat. Nos. 5,521,291 and 5,547,932). Typically, gene delivery involves exposing a cell to a gene delivery mixture that includes preselected genetic material together with an appropriate vector, mixed, for example, with an effective amount of lipid transfecting agent (lipofection). The amount of each component of the mixture is chosen so that gene delivery to a specific species of cell is optimized. Such optimization requires no more than routine experimentation. The ratio of DNA to lipid is broad, preferably about 1:1, although other proportions may also be utilized depending on the type of lipid agent and the DNA utilized. This proportion is not crucial. Other well known gene delivery methods include electroporation or chemical methods. (E.g., M. Ostresh, *No barriers to entry: transfection tools get biomolecules in the door*, The Scientist 13(11):21–23 [1999]).

"Gene delivery agent", as used herein, means a composition of matter added to the genetic material for enhancing the uptake of exogenous DNA segment(s) into a mammalian cell. The enhancement is measured relative to the uptake in the absence of the gene delivery agent. Examples of gene delivery agents include adenovirus-transferrin-polylysine-DNA complexes. These complexes generally augment the uptake of DNA into the cell and reduce its breakdown during its passage through the cytoplasm to the nucleus of the cell.

An immunoliposome transfection method is a preferred means of gene delivery. Other preferred methods also yield high transfection efficiency, such as Ca-coprecipitation, or transfection using gene delivery agents such as Lipofectamine (Life Technologies), or Fugene-6 (Boehringer Mannheim, Inc.). Other preferred gene delivery agents include Lipofectin®, DMRIE C, Cellfectin® (Life Technologies), LipoTAXI (Stratagene), Superfect or Effectene (Qiagen). Although these are not as efficient gene delivery agents as viral agents, they have the advantage that they facilitate stable integration of xenogeneic DNA sequence into the vertebrate genome, without size restrictions commonly associated with virus-derived gene delivery agents. But a virus, or transfecting fragment thereof, can be used to facilitate the delivery of the genetic material into the cell. Examples of suitable viruses include adenoviruses, adeno-associated viruses, retroviruses such as human immunodeficiency virus, other lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of cells and mixtures thereof. All of the above viruses may require modification to render them non-pathogenic or less antigenic. Other known viral vector systems are also useful.

The transfection step is followed by expressing, or over-expressing, at least one of the neurogenic transcription factors, while simultaneously, or near simultaneously, deactivating factors that are responsible for suppressing neuronal differentiation. This latter step is accomplished by adding to the growth medium at least one antisense oligonucleotide known to suppress neuronal differentiation, such as the human MSX1 gene and/or the human HES1 gene (or non-human, homologous counterparts), and growing the cells.

Thus, the transfected epidermal basal cell(s) are grown in the presence of at least one antisense oligonucleotide comprising a nucleotide sequence of a segment of a human MSX1 gene and/or a nucleootide sequence of a segment of a human HES1 gene, or homologous non-human counterpart of either of these, in an amount sufficient to suppress the expression of functional gene product of MSX1 or HES1. A sufficient amount of antisense oligonucleotides directed to suppressing transcription of both MSX1 and HES1 is a concentration in the medium of about 5 to 10 µM each. Examples of useful antisense oligonucleotide sequences include the following human MSX1 antisense oligonucleotide sequences:

5'-GACACCGAGTGGCAAAGAAGTCATGTC-3' (first methionine) (MSX1-1; SEQ. ID. NO.:13) or 5'-CGGCTTCCTGTGGTCGGCCATGAG-3' (third methionine) (MSX1-2; SEQ. ID. NO.:14); and two antisense oligonucleotides corresponding to the human HES1 open reading frame 5' sequence:

5'-ACCGGGGACGAGGAATTTTTCTCCAT-TATATCAGC-3' (HES1-1; SEQ. ID. NO.:15) or HES1 open reading frame middle sequence 2:

5'-CACGGAGGTGCCGCTGTTGCTGGGCTG-GTGTGGTGTAGAC-3' (HES1-2; SEQ. ID. NO.:16). Other oligonucleotide sequences are also useful as long as they will hybridize to nucleic acids comprising at least a segment of a human or homologous non-human MSX1 gene (e.g., GenBank Accession Nos. M97676 [human]; NM 002448 [human]; X62097 [chicken]; D82577.1 *[Ambystoma mexicanum]*) or at least a segment of an HES1 gene (e.g., GenBank Accession Nos. Y07572 [human]; Q04666 [rat]; P35428 [mouse]; AB019516 [newt]; AB016222 *[Saccharomyces pombe]*; U03914 *[Saccharomyces cerevisiae]*), preventing expression of functional MSX1 and/or HES1 gene products by targeting (i.e., hybridizing with) MSX1 or HES1 nucleic acids. The skilled artisan can readily find other useful MSX1 and/or HES1 oligonucleotide sequences by conducting a sequence similarity search of a genomics data base, such as the GenBank database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine server. (E.g., Altchul, S. F., et al., *Gapped BLAST and PSI-BLAST: a new generation of protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996]; Altschul, S. F., et al., *Basic local alignment search tool*, J. Mol. Biol. 215(3):403–10 [1990]).

Preferably, one or more nucleotide residues of the antisense oligonucleotides is thio-modified by known synthetic methods, used by the practitioner or by a commercial or other supplier, to increase the stability of the oligonucleotides in the culture media and in the cells. (E.g., L. Bellon et al., 4'-*Thio-oligo-beta-D-ribonucleotides: synthesis of beta-4'-thio- oligouridylates, nuclease resistance, base pairing properties, and interaction with HIV-1 reverse transcriptase*, Nucleic Acids Res. 21(7):1587–93 [1993]; C. Leydier et al., 4'-*Thio-RNA: synthesis of mixed base 4'-thio-oligoribonucleotides, nuclease resistance, and base pairing properties with complementary single and double strand*, Antisense Res. Dev. 5(3):167–74 [1995]).

During the growing of the transfected cells, exposure to the antisense oligonucleotides is for a period long enough for MSX1 and/or HES1 proteins pre-existing in the growing cells to be degraded. For particular proteins with a relatively short half-life, the exposure period necessary is only a matter of hours to one day. Proteins with relatively long half-life require longer treatments with antisense oligonucleotides. An exposure period of about two to three days generally suffices. The further course of development of the transdifferentiated cells depends on the in situ environmental cues to which they are exposed, whether in vitro, or implanted in vivo. Optionally, the transdifferentiated cell(s) are grown in a medium including a retinoid compound, such as retinoic acid or Vitamin A, and optionally a nerve growth factor or neurotrophin, such as brain-derived neurotrophic factor (BDNF), ciliary neurotrophic factor (CNTF), platelet-derived growth factor (PDGF), nerve growth factor (NGF), neurotrophin (NT)-3, neurotrophin (NT)-4, or sonic hedgehog (Shh), and/or functional fragments of any of these. For example, treating newly formed neuronal cells with all-trans retinoic acid and BDNF results in development of GABAergic neurons or neuron-like cells (that express Neurofilament M), whereas treatment with glial-conditioned media and sonic hedgehog aminoterminal peptide (Shh-N) results in development of mostly dopaminergic neuronal cells. Treatment with Shh-N promotes the differentiation of neuronal and oligodendroglial species from nestin-immunoreactive cells (uncommitted neural progenitor cells) and inhibits the antiproliferative, astroglial-inductive, oligodendroglial-suppressive effects of BMP2. (E.g., G. Zhu et al., *Sonic hedgehog and BMP2 exert opposing actions on proliferation and differentiation of embryonic neural progenitor cells*, Dev. Biol. 21591):118–29 [1999]). This plasticity in response to the environmental cues allows the cells to maintain neuronal differentiation in vitro or in situ, when implanted into the mammalian subject, without the further addition of antisense oligonucleotides.

In accordance with the method, expression of any neural progenitor-specific, neural-specific, and/or glial specific marker is detected by conventional biochemical or immunochemical means. Preferably, immunochemical means are employed, such as, but not limited to, enzyme-linked immunosorbent assay (ELISA), immunofluorescent assay (IFA), immunoelectrophoresis, immunochromatographic assay or immunohistochemical staining. These methods employ marker-specific polyclonal or monoclonal antibodies or antibody fragments, for example Fab, Fab', F(ab')$_2$, or F(v) fragments, that selectively bind any of various neural progenitor, neuronal or glial cell antigens. Antibodies targeting individual specific markers are commercially available and are conveniently used as recommended by the antibody manufacturers. Markers specific to neural progenitor, neuronal, or glial cells include antigenic molecules that indicate expression of, for example, nestin, neural RNA-binding protein Musashi, neurofilament M (NF-M; Sigma, Inc.), neural-specific tubulin (Sigma, Inc.), neural-specific enolase (Incstar, Inc.), microtubule associated protein 2 (MAP2, Boehringer Mannheim), glial fibrillary acidic protein, O4, or any other detectable marker specific to a neural progenitor, neuronal or glial cell.

Alternatively, expression of neural progenitor-specific, neural-specific or glial-specific markers is detected by conventional molecular biological techniques for amplifying and analyzing mRNA transcripts encoding any of the markers, such as but not limited to reverse transcriptase-mediated polymerase chain reaction (RT-PCR), transcription-mediated amplification (TMA), reverse transcriptase-mediated ligase chain reaction (RT-LCR), or hybridization analysis. Nucleic acid sequences encoding markers (e.g., nestin, neural RNA-binding protein Musashi, neurofilament M, neural-specific tubulin, neural-specific enolase, microtubule associated protein 2, glial fibrillary acidic protein, 04) specific to neural progenitor, neuronal or glial cells are known and available in databases such as GenBank. The skilled artisan can readily determine other useful marker-specific sequences for use as primers or probes by conducting a sequence similarity search of a genomics data base, such as the GenBank database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine server. (E.g., Altchul, S. F., et al., *Gapped BLAST and PSI-BLAST: a new generation of protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996]; Altschul, S. F., et al, *Basic local alignment search tool*, J. Mol. Biol. 215(3):403–10 [1990]).

Optionally, morphological criteria are additionally used to detect transdifferentiation of epidermal basal cells into neurons or neuron-like cells. For example, neurons or neuron-like cells may express neurites, or neurite-like processes, longer than three cell diameters (about 50 microns or longer).

The present invention also relates to a transdifferentiated cell of epidermal origin having a morphological, physiological and/or immunological feature of a neural progenitor, neuronal, or glial cell. The inventive cell can be, but is not necessarily, produced by the inventive method of transdifferentiating an epidermal basal cell into a cell having one or more morphological, physiological and/or immunological features of a neural progenitor, neuronal, or glial cell (astrocyte, oligodendrocyte, or microglia). The cell includes cultured cellular progeny of a cell transdifferentiated from an epidermal basal cell.

"Neural progenitor" is an ectodermally-derived pluripotent stem cell having, as a physiological feature, a capacity, under physiological conditions that favor differentiation (e.g., presence of particular neurotrophic factors), to develop one or more morphological, physiological and/or immunological features specifically associated with a neuronal or glial cell type, i.e., neurons, astrocytes (i.e., astroglia), oligodendrocytes (i.e., oligodendroglia), and microglia. For example, bipotent neural progenitor cells differentiate into astrocytes after exposure to ciliary neurotrophic factor (CNTF), or into neuronal cells after exposure to platelet-derived growth factor (PDGF). (E.g., J. K. Park et al., *Bipotent cortical progenitor cells process conflicting cues for neurons and glia in a hierarchical manner*, J. Neurosci. 19(23):10383–89 [1999]). Some neural progenitors are "neural restricted" progenitors, which can differentiate only into neurons.

The presence of neural progenitors can be detected by functional testing under suitable physiological conditions to determine the course of development and differentiation into neuronal or glial cells. Preferably, neural progenitor cells are identified by detecting the expression of any of several well-defined specific markers, such as the cytoskeletal protein nestin and/or neural RNA-binding protein Musashi (MSI). (E.g., T. Nagata et al., *Structure, backbone dynamics and interactions with RNA of the C-terminal RNA-binding domain of a mouse neural RNA-binding protein, Musashi* 1, J. Mol. Biol. 287(2):315–30 [1999]; P. Good et al., *The human Musashi homolog* 1 (MSI1) *gene encoding the homologue of Musashi/Nrp-*1, *a neural RNA-binding protein putatively expressed in CNS stem cells and neural progenitor cells*, Genomics 52(3):382–84 [1998]; S. Sakakibara et al., *Mouse-Musashi-*1, *a neural RNA-binding protein highly enriched in the mammalian CNS stem cell*, Dev. Biol. 176(2):230–42 [1996]).

"Neuronal" cells, or "neuron-like" cells, include cells that display one or more neural-specific morphological, physiological and/or immunological features associated with a neuronal cell type, including sensory neuronal, motoneuronal, or interneuronal cell types. The practitioner can choose, in connection with a particular application, the operative criteria or subset of specific features used for determining whether a transdifferentiated cell belongs to a particular type of neuronal population. Useful criterial features include morphological features (e.g., long processes or neurites); physiological and/or immunological features, such as expression of a set of neural-specific markers or antigens (e.g., neurofilament M, neural-specific β-tubulin, neural-specific enolase, microtubule associated protein 2, or others); synthesis of neurotransmitter(s) (e.g., dopamine; expression of tyrosine hydroxylase—the key enzyme in dopamine synthesis; or gamma aminobutyric acid [GABA]); the presence of receptors for neurotransmitter(s); and/or physiological features such as membrane excitability and/or developmental response to particular cytokines or growth factors. An advantage of the transdifferentiated cell(s) of the invention is that it can be manipulated, in vitro in the presence of specific exogenously supplied signal molecules, or in vivo within specific microenvironments, into diverse neuronal types as defined by the practitioner's operative criteria.

A glial cell or "glial-like" cell includes a cell that has one or more glial-specific features, associated with a glial cell type, including a morphological, physiological and/or immunological feature specific to a glial cell (e.g. astrocytes or oligodendrocytes), for example, expression of the astroglial marker fibrillary acidic protein (GFAP) or the oligodendroglial marker O4.

In one embodiment, the transdifferentiated cell exhibits a lack of mitotic activity under cell culture conditions which induce differentiation in neural progenitor cells, such as nutrient-rich medium containing neurotrophins (e.g., DMEM/F12, plus neuronal growth supplement B27 [Gibco-BRL], $10^{-7}$ M all-trans retinoic acid and brain derived neurotrophic factor [BDNF; 20 ng/mL], at 37° C. in an atmosphere containing 5% $CO_2$).

In other embodiments, the cell is a GABAergic cell, i.e., a cell that produces gamma aminobutyric acid, the predominant inhibitory neurotransmitter in the central nervous system. For example, treating the transdifferentiated cells plated on laminin coated surface with all-trans retinoic acid ($10^{-7}$ M) and BDNF (10 ng/mL) for 5–15 days results in development of GABAergic neurons or neuron-like cells.

In still other embodiments, the transdifferentiated cell is a dopaminergic cell, i.e., a cell that produces dopamine, a catecholamine neurotransmitter and hormone. These cells result from post-transdifferentiation treatment with glial conditioned media and sonic hedgehog aminoterminal peptide.

In one embodiment, the transdifferentiated cell has a morphological, physiological and/or immunological feature of an glial cell, such as expression of glial fibrillary acidic protein (GFAP).

It is a benefit of the inventive transdifferentiated cell(s) that they can be implanted into, and/or grafted to, a patient in need for use in cell therapy or gene therapy approaches to neurological injury or disease. Advantageously, the transdifferentiated cell(s) can be used directly without requiring a step for cell expansion.

The present invention also relates to a cell culture derived from the inventive transdifferentiated cell(s) originated from epidermal basal cells. The cell culture contains a plurality of cells that have a morphological, physiological and/or immunological feature of a neural progenitor, neuronal, or glial cell, for example, expression of one or more specific marker(s). The cell culture is maintained under culture conditions that favor the in vitro propagation of neural progenitors, neuronal, or glial cells, for example, suitable temperature, pH, nutrients, and growth factors, as known in the art. The cell culture can be manipulated to express additional or different neural-specific or glial specific-markers in the presence of specific exogenously supplied signal molecules.

The features and properties of the transdifferentiated cells and cell cultures of the present invention make them viable as a fundamental biotechnology tool directed to the human nervous system. Moreover, the transdifferentiated cells and cell cultures of the invention meet the technical criteria for use in cell and gene therapies directed to nervous system disease and disorders. First, the inventive transdifferentiated cells and cell cultures can display morphological and functional features of neurons: they can develop long neurites with a growth cones at the end, they express a number of neural specific genes, and they do not continue to proliferate in conditions which induce differentiation. Therefore, for use in gene therapy and cell therapy, the transdifferentiated cells can not only deliver a single potential gene or factor, but additionally are capable of furnishing the whole infrastructure for nerve regeneration.

Second, the cultured transdifferentiated cells can be propagated as multipotential nervous system progenitor cells in conditions that favor proliferation and do not induce differentiation. Hence, these progenitor cells retain the capacity to become many different types of neurons or neuron-like cells depending upon the environmental cues to which they are exposed, for example GABAergic or dopaminergic cells. This broad plasticity suggests that, once implanted, the cells of the present invention will retain the capacity to conform to many different host brain regions and to differentiate into neurons specific for that particular host region. These intrinsic properties of the transdifferentiated neurons are different from the existing tumorigenic cell lines, where some neuronal differentiation can be induced under artificial conditions.

Third, another advantage of the inventive transdifferentiated cells and cell cultures is that there is no need for cell expansion, as is required with stem cell technology used to generate neurons for cell and gene therapies. Thus, the transdifferentiated cells of the present invention are sufficient in number (several millions of cells) for direct implantation. In summary, the unique characteristics and properties of these transdifferentiated cells and cell cultures yield an invention of significant scientific and commercial potential.

Consequently, the present invention also relates to a method of delivering locally secretable regulatory factors in vivo within the nervous system of a mammalian subject, including a human. The method involves transdifferentiating a population of epidermal basal cells from the subject, in accordance with the inventive method described above, into cells having a morphological, physiological and/or immunological feature of a neuronal cell. Epidermal basal cells of the particular subject requiring treatment with secretable regulatory factors are preferred, in order to avoid transplant rejection. Before, during, or after the transdifferentiation step, the cells are genetically modified, in vitro, by known methods as described above, with an expression vector comprising a DNA encoding a predetermined secretable regulatory factor, a biochemical precursor thereof, or an enzyme that catalyzes the biosynthesis of either the factor or a precursor, and the genetically modified cells are selected, cultured, and implanted into the subject. Transfecting or otherwise genetically modifying the cells involves delivery of an expression vector comprising the DNA encoding the predetermined secretable regulatory factor, a precursor thereof, or an enzyme that catalyzes the biosynthesis of either the factor or a precursor. Expression of the gene for the regulatory factor, precursor, or enzyme is under the transcriptional control of a neuronal specific promoter (for example, neurofilament promoter or neural-specific enolase promoter). Enhanced secretion of the regulatory factor by the genetically modified cells results. This does not depend on the formation of functional interneuronal connections such as those that transmit electrochemical sensory, motor, or cognitive signals.

Examples of secretable regulatory factors include dopamine and neurotrophic factors, such as nerve growth factor (NGF), brain-derived growth factor (BDGF), neurotrophin-3, neurotrophin-4, insulin-like growth factor, ciliary neurotrophic factor (CNTF), or glia-derived neurotrophic factor. Nervous system disorders that can be treated using the method include Alzheimer's disease, diabetic neuropathy, taxol neuropathy, compressive neuropathy, AIDS-related neuropathy, amyotrophic lateral sclerosis, large fiber neuropathy, vincristine neuropathy, and Parkinson's disease.

Implantation of the genetically modified transdifferentiated cells is by conventional methods (e.g., stereotactic injection). Implantation is into an appropriate site within the nervous system of the subject, depending on the particular disorder being treated.

By way of example, the method is advantageous in the treatment of Parkinson's disease, which results mainly from degeneration of dopamine releasing neurons in the substantia nigra of the brain and the subsequent depletion of dopamine neurotransmitter in the striatum. The cause of this degeneration is unknown, but the motor degeneration symptoms of the disease can be alleviated by peripherally administering the dopamine precursor, L-dopa, at the early onset of the disease. As the disease continues to worsen, L-dopa is no longer effective, and currently, no further treatment is available. One promising treatment being developed is to transplant dopamine-rich substantia nigra neurons from fetal brain into the striatum of the brain of the patient. Results obtained from various clinical studies look extremely optimistic, however, it is estimated that up to 10 fetal brains are needed to obtain a sufficient number of cells for one transplant operation. This requirement renders unfeasible the wide application of the transplantation of primary fetal neurons as a therapeutic treatment modality. This problem is resolved, however, by utilizing the transdifferentiated neurons or neuron-like cells of the present invention for treatment of Parkinson's disease.

It is now widely recognized that transplantation of dopamine producing cells is the most promising therapy of treating severe Parkinson's disease. Stable cell populations or cell lines genetically modified to produce dopamine is essential to an effective therapy. Since tyrosine hydroxylase (TH) is the key enzyme for dopamine biosynthesis, cloning the TH gene into an appropriate expression vector is a first step in the method of treatment. Human TH cDNA is cloned into a eukaryotic expression vector. After gene delivery, clones of genetically modified cells that demonstrate stable integration of the expression vector are selected for implantation purposes. Thus, transdifferentiated cells of the present invention are produced with enhanced expression of the tyrosine hydroxylase (TH) gene.

These cells are implanted into the patient's striatum or brain. The cells are typically implanted bilaterally in the caudate nucleus and putamen by using Magnetic Resonance Imaging (MRI)-guided stereotactic techniques. A stereotactic frame is affixed to the skull after administration of local anesthesia. The caudate nucleus and putamen are then visualized with MRI. Thereafter, under general anesthesia, about 10 passes with very thin stereotactic needles are made bilaterally, 4 mm apart in the caudate and putamen. The rationale for track spacing at approximately 4 mm intervals is important because fetal dopamine neuron processes grow several millimeters, reinnervating the host's striatum. Four trajectories for needle tracks in the caudate and six tracks in the putamen are calculated to avoid the posterior limb of the internal capsule. The entry points for the putamen and caudate tracks are at two different sites on the surface of the brain. The tracks to the putamen are approximately vertical with reference to a coronal plane, while the approach to the caudate is at an angle of approximately 30 degrees. After the implantation surgery, the implanted cells secrete dopamine in situ alleviating the subject's Parkinson's disease symptoms.

The present invention also relates to a method of isolating or identifying a novel nerve growth (or neurotrophic) factor that employs transdifferentiated cells of the invention. The methods involve transdifferentiating a population of proliferating epidermal basal cells into neuronal progenitor cells, neuronal cells, or glial cells; culturing the transdifferentiated cells; exposing the cultured cells, in vitro, to a potential nerve growth factor; and detecting the presence or absence of an effect of the potential nerve growth factor on the survival of the cells or on a morphological or electrophysiological characteristic and/or molecular biological property of the cells. The transdifferentiated cells are assayed in vitro to determine whether there is an effect of a potential nerve growth factor on a physiological or molecular biological property of the transdifferentiated cells. For example, which, if any, neuronal or glial cell types develop from neural progenitors, the maturation of particular cell types, and the continued support of cell survival (e.g., effect on cell numbers) can be determined. In addition, experimental techniques, based on an electrophysiological characteristic (patch clamp, different types of intracellular recording, etc.) or molecular biological properties (gene expression profiles, organization of cytoskeleton, organization of ion channels and receptors etc.) can be used to detect the effects of potential nerve growth/neurotrophic factors on particular cell types. The potential factor can be, but need not be an isolated compound; the inventive transdifferentiated cells can be used to test, or assay, the effect, or lack thereof, of potential growth factor sources (tissue homogenates, expression cDNA library products, etc.) on the survival and functional characteristics of the cells to detect candidates for further isolation.

The use of transdifferentiated epidermal basal cells bypasses the difficulties in isolating and culturing neuronal cell types from the brain, and, therefore, the inventive method of identifying a novel nerve growth factor is a benefit to research in this area.

This same advantage pertains to the inventive method of using cells transdifferentiated from epidermal basal cells to identify a potential chemotherapeutic agent (i.e., a drug) by transdifferentiating a population of epidermal basal cells into neuronal progenitor, neuronal, or glial cells by the inventive method described above; culturing the transdifferentiated cells; exposing the cultured cells, in vitro, to a potential chemotherapeutic agent; and detecting the presence or absence of an effect of the potential chemotherapeutic agent on the survival of the cells or on a morphological or electrophysiological characteristic and/or molecular biological property of said cells. An effect altering cell survival, a morphological or electrophysiological characteristic and/or a molecular biological property of the cells indicates the activity of the chemotherapeutic agent. The potential chemotherapeutic agent can be an agent intended to treat a nervous system disorder, or the method can be used to test an agent intended or proposed for treating any other type of disorder for its effects on cells possessing neural progenitor, neuronal or glial cell features. Experimental assay techniques, based on an electrophysiological characteristic (patch clamp, different types of intracellular recording, etc.) or molecular biological properties (gene expression profiles, organization of cytoskeleton, organization of ion channels and receptors etc.), as well as cell survival, can be used to detect the effects of potential chemotherapeutic agents on particular cell types. The potential chemotherapeutic agent can be, but need not be an isolated compound; the inventive transdifferentiated cells can be used to test, or assay, the effect of potential chemotherapeutic agents (tissue homogenates, expression cDNA library products, etc.) on the survival and functional characteristics of the cells to detect candidates for further isolation and development. Since epidermal basal cells transdifferentiated into neurons or neuron-like cells in culture can express several neurotransmitters and receptor complexes, cell lines derived from these cells can be developed which, when differentiated into mature neurons, would display a unique profile of neurotransmitter receptor complexes. Such neuronal cell lines can be valuable tools for designing and screening potential chemotherapeutic agents.

The present invention also relates to a method of using transdifferentiated cells or cell cultures to screen a potential chemotherapeutic agent to treat a nervous system disorder of genetic origin, for example, Alzheimer's disease. The method is practiced in accordance with the above-described method of screening a potential chemotherapeutic agent, however, epidermal basal cells derived from a human subject diagnosed with a particular nervous system disorder of genetic origin are transdifferentiated and the effect of the potential chemotherapeutic agent on a physiological or molecular biological property of the transdifferentiated cells is assayed in vitro. Different types of neuronal cells derived from transdifferentiated epidermal basal cells of the present invention will provide novel methodologies to screen potential chemotherapeutic agents. For example, using the epidermal basal cells from patients with genetic defects that affect the nervous system will make it possible to manipulate environmental cues to induce the development of various types of neuronal cell populations that also carry this genetic defect. These cells can be used for screening of chemotherapeutic agents which potentially have effect on the diseased neurons or neuron-like cells displaying a specific set or profile of neurotransmitters, receptors complexes, and ion channels.

Regardless of whether under a particular set of environmental conditions, in vitro, the inventive transdifferentiated cells express all the biochemical, morphological, and functional characteristics of a given neuronal population in vivo, they provide at least useful simulations of neurons for identifying, screening, or isolating promising new drugs or neural growth factors. Once the potential of a chemical agent is identified by the inventive methods, then, further research can be done to verify its actual effect on particular cell populations of the nervous system and ascertain its clinical usefulness. Thus, the inventive methods of screening a potential chemotherapeutic agent are of benefit in finding and developing the next generation of pharmaceutical drugs narrowly aimed at modifying specific brain functions.

The present invention also relates to a kit for transdifferentiating an epidermal basal cell into a cell having one or more morphological, physiological and/or immunological feature(s) of a neural progenitor, neuronal, or glial cell. The kit is an assemblage of materials for facilitating the transdifferentiation of epidermal basal cells in accordance with the inventive methods.

The inventive kit preferably includes the following expression vectors and reagents: one or more expression vector(s) containing cDNA(s) encoding a neurogenic transcription factor, or fragment(s) thereof, such as NeuroD1, NeuroD2, ASH1, Zic1, Zic3, and MyT1, or non-human, homologous counterparts, at least one antisense oligonucleotide corresponding to a segment or portion of the human MSX1 gene and/or the human HES1 gene, or non-human, homologous counterparts, a retinoid and at least one neurotrophin, such as BDNF, CNTF, PDGF, NGF, NT-3, NT-4, and/or sonic hedgehog, or an active fragment of any of these. Preferably but not necessarily, the kit contains instructions for using the kit components for transdifferentiating a mammalian subject's epidermal basal cells, for example, starting with a patient's own skin cells.

The materials or components assembled in the inventive kit can be provided to the practitioner stored in any convenient and suitable ways that preserve their operability and utility. For example the components can be in dissolved, dehydrated, or lyophilized form; they can be provided at room, refrigerated or frozen temperatures. The kits of the present invention preferably include instructions for using the materials or components effectively for practicing any or all of the inventive methods.

The foregoing descriptions of the methods, transdifferentiated cells, cell cultures, and kits of the present invention are illustrative and by no means exhaustive. The invention will now be described in greater detail by reference to the following non-limiting examples.

EXAMPLE I

Preparation of Epidermal Cell Culture and Dedifferentiation

Human adult skin was obtained from surgery procedures or skin biopsy. Before cultivation, as much as possible of the subepidermal tissue was removed by gentle scraping. Primary cultures were initiated by culturing 4–10 2×2 mm explants/35 mm tissue culture dish in Dulbecco's modified Eagle medium (GIBCO-BRL, Life Technologies, Inc.) with 15% fetal calf serum (GIBCO-BRL, Life Technologies, Inc.), 0.4 µg/ml hydrocortisone, and 10 ng/ml epidermal growth factor (Collaborative Research, Inc.). The medium was changed every three days. Thirty to thirty-five day old cultures were used for subsequent experimentation. Before transfections and further treatment, differentiated cell layers were stripped off by incubating the cultures in $Ca^{2+}$-free minimal essential medium (GIBCO-BRL, Life Technologies, Inc.). Generally, a calcium free media contains less than $10^{-6}$ M $Ca^{2+}$ ions. After 72 hours, suprabasal layers were detached and removed after shaking of the culture dish. This calcium free treatment also dedifferentiates epidermal basal cells, as they loose expression of cytokeratines which are characteristic of epidermal cells. The cultures were then refed medium with normal $Ca^{2+}$ concentration, that is, 2 mM calcium ions containing all the additives, that is, FCS (15%), hydrocortisone (0.4 µg/ml), EGF (10 ng/ml), and cultured 18–24 hours at 37° C. in an atmosphere containing 5% $CO_2$.

EXAMPLE II

Transfections of Cultured Epidermal Cells

Epidermal basal cells were transfected using a Ca-coprecipitation protocol (GIBCO-BRL, Life Technologies, Inc.), Lipofectamine reagent (GIBCO-BRL, Life Technologies, Inc.), and immunoliposomes (Holmberg et al., 1994). Ca-coprecipitation and Lipofectamine reagent were used as indicated by manufacturer. Ten µg of either pRcCMVneo eukaryotic expression vector (Invitrogen) alone, or cloned pRcCMVneo vectors containing either B-galactosidase (CMV-β-gal), NeuroD1 (CMV-ND1), NeuroD2, (CMV-ND2), hASH1 (CMV-hASH1), Zic1 (CMV-Zic1), or hMyT1 (CMV-MyT1) cDNAs were used to transfect cells in one 35 mm tissue culture dish. All the cDNAs were cloned in our laboratory using sequence information from GenBank: Accession numbers: hNeuroD1 D82347 (SEQ. ID. NOS.:1 and 7); U50822 (SEQ. ID. NOS.:2 and 8); hNeuroD2 U58681 (SEQ. ID. NOS.:3 and 9); hASH1 L08424 (SEQ. ID. NOS.:4 and 10); hZic1 D76435 (SEQ. ID. NOS.:5 and 11); hMyT1 M96980 (SEQ. ID. NOS.:6 and 12). All of the cloned genes were of human origin.

Oligonucleotide primers were designed based on the sequences of interest and used to amplify full length cDNAs using RT-PCR techniques and human fetal brain mRNA as a template. Also, NeuroD1, NeuroD2 and hASH1 cDNAs were isolated by screening the human fetal brain cDNA library (Stratagene). All cDNA sequences were verified by sequencing and in-vitro translation using reticulocyte lysate an in-vitro translation system (Amersham).

EXAMPLE III

Preparation and Use of Antisense Oligonucleotides

Human MSX1 antisense oligonucleotides sequences 1) 5'-GACACCGAGTGGCAAAGAAGTCATGTC (first methionine) (MSX1-1; SEQ. ID. NO.:13); and 2) 5'-CGGCTTCCTGTGGTCGGCCATGAG (third methionine) (MSX1-2; SEQ. ID. NO.:14) were synthesized. Additionally, human full length HES1 cDNA from the human fetal brain cDNA library was isolated and sequenced (Stratagene). Two antisense oligonucleotides corresponding to the human HES1 open reading frame 5' sequence 1) 5'-ACCGGGGACGAGGAATTTTTCTCCATTATATCAGC (HES1-1; SEQ. ID. NO.:15) and middle sequence 2) 5'-CACGGAGGTGCCGCTGTTGCTGGGCTGGTGTGGTGTAGAC (HES1-2; SEQ. ID. NO.:16) were synthesized. The preferred antisense oligonucleotides are thio-modified by known methods. Therefore, thio-modified versions of these oligonucleotides corresponding to human MSX1 and human HES1 were synthesized and used to increase the stability of oligunucleotides in the culture media and in the cells.

In the experimental protocol, described below, oligonucleotides were directly added to the culture media at the concentration of 5–10 µM. Randomly synthesized oligonucleotides and oligonucleotides corresponding to the sequence of human albumin were used as controls.

EXAMPLE IV

Analytical Method to Detect Transdifferentiation

Immunohistochemical detection of neurofilament M expression was chosen as one marker for neuronal differentiation. Cells were fixed with 4% paraformaldehyde and processed according to the immunohistochemical detection protocol recommended by the antibody manufacturer (Sigma, Inc.). Neurofilament M positive cells were counted by fluorescent microscopy. Several additional antibodies to neuronal antigens were used to characterize, in more detail, the nature of basal cell transdifferentiation into neurons. Antibodies against neural specific tubulin (Sigma, Inc.), neural specific enolase (Incstar, Inc.), microtubule associated protein 2 (MAP2, Boehringer Mannheim), and neurofilaments Mix (Sternberger) were used as recommended by the antibody manufacturer. Antibodies against glial fibrillary acidic protein (GFAP, Incstar) were used to detect differentiation of astrocytes from epidermal basal cells. Additionally, morphological criteria were used to detect transdifferention of epidermal basal cells into neuronal cells. Cells with neurites, or processes, longer than three cell diameters (50 microns or longer), and expressing at least one neuronal marker (antigen), were counted as neurons.

EXAMPLE V

Transdifferentiation Protocol and Experimental Results

Various combinations of neural regulators leading to expression, or over-expression, of neurogenic bHLH and/or Zn-finger transcription factors and substantially simultaneous suppression of MSX1 and/or HES1 expression were tested to ascertain their effect on transdifferentiation of epidermal basal cells. Results of these experiments are presented in Table I.

For these experiments, a immunoliposome transfection method is preferred, since it resulted in the highest transfection efficiency. Other methods of transfection that yield high transfection efficiency, such as Ca-coprecipitation, Lipofectamine, or Fugene-6 (Boehringer Mannheim, Inc.), known in the art, can be used instead of immunoliposomes. After transfection and antisense oligonucleotide treatments, cells were grown in the presence of all-trans retinoic acid ($10^{-7}$M) and BDNF (20 ng/ml) for 5 days before immunostaining.

Table 1 shows the results of the transdifferentiation procedures described above leading to the conversion of epidermal basal cells into neuronal Neurofilament M-expressing cells in-vitro. Various combinations of simultaneous expression, or near simultaneous expression, of neurogenic bHLH and/or Zn-finger transcription factors and suppression of expression of MSX1 and/or HES1 genes were used to initiate transdifferentiation. Neurofilament M immunostaining and evaluation of the length of neurites, or processes (50 microns or longer were counted as neurites) were used to identify neuronal cells. Controls using pRCMV vector plasmid and randomly synthesized oligonucleotides, and oligonucleotides corresponding to the sequence of human albumin, showed no transdifferentiation of epidermal basal cells. Cells expressing Neurofilament M were counted by fluorescent microscopy. Five to seven fields of immunostained cells were counted for each treatment, each field containing 100–300 cells.

TABLE I

TRANSDIFFERENTIATION OF EPIDERMAL BASAL CELLS

| TREATMENT | % NEURONAL CELLS (i.e., % Neurofilament M expressing) |
|---|---|
| control, no treatment: | 0 |
| Over-expression: | |
| NeuroD1 | 0.01 |
| NeuroD2 | 0.03 |
| ASH1 | 0 |
| Zic1 | 0 |
| MyT1 | 0 |
| NeurcD1 + Zic1 | 0.04 |
| NeuroD2 + Zic1 | 0.05 |
| NeuroD1 + NeuroD2 + Zic1 | 0.05 |
| NeuroD1 + MyT1 | 0.02 |
| NeuroD2 + MyT1 | 0.03 |
| NeuroD1 + NeuroD2 + MyT1 | 0.05 |
| NeuroD1 + NeuroD2 + MyT1 + Zic1 | 0.05 |
| Antisense oligonucleotides: | |
| MSX1-1 | 0 |
| MSX1-2 | 0 |
| HES1-1 | 0 |
| HES1-2 | 0 |
| MSX1-1 + MSX1-2 + HES1-1 + HES1-2 | 0 |

TABLE I-continued

TRANSDIFFERENTIATION OF EPIDERMAL BASAL CELLS

| TREATMENT | % NEURONAL CELLS (i.e., % Neurofilament M expressing) |
|---|---|
| Combination of antisense oligonucleotides and over-expression of neurogenic factors: | |
| NeuroD1 + NeuroD2 + MSX1-1 + MSX1-2 | 0.5 |
| NeuroD1 + NeuroD2 + HES1-1 + HES1-2 | 0.8 |
| NeuroD1 + NeuroD2 + MSX1-1 + HES1-1 | 7 |
| Zic1 + MSX1-1 + MSX1-2 | 0.05 |
| Zic1 + HES1-1 + HES1-2 | 3 |
| MyT1 + MSX1-1 + MSX1-2 | 0.01 |
| MyT1 + HES1-1 + HES1-2 | 0.5 |
| MyTI + MSX1-1 + HES1-1 | 0.9 |
| NeuroD1 + Zic1 + MSX1-1 | 11 |
| NeuroD1 + Zic1 + MSX1-1 + HES1-1 | 20 |
| NeuroD1 + MyT1 + MSX1-1 | 10 |
| NeuroD1 + MyT1 + MSX1-1 + HES1-1 | 26 |
| NeuroD1 + Zic1 + MyT1 + MSX1-1 + HES1-1 | 25 |

In summary, transdifferentiation of epidermal cells into neurons is best achieved by the combined effect of expressing neurogenic transcription factors, which positively regulate neuronal differentiation, and antisense oligonucleotides, corresponding to negative regulators of neuronal differentiation. The experimental data indicate that a preferred method of transdifferentiation of epidermal cells into neurons includes the expression of both a bHLH and zinc finger transcription factor, which positively regulate neuronal differentiation, in the presence of at least one antisense DNA, corresponding to a negative regulator of epidermal differentiation. Additionally, the expression of two bHLH transcription factors in the presence of two negative regulator antisense DNAs yielded a fairly high percentage of differentiated neurons.

EXAMPLE VI

Characterization of the Transdifferentiated Neuronal Cells

To further evaluate the transdifferention process and nature of newly formed neuronal cells, expression of several neuronal marker genes in these cells using immunostaining with specific antibodies against neuronal marker proteins were analyzed. In these experiments, the following combinations of transfection of neurogenic genes and antisense oligonucleotide treatments were used:

NeuroD1+Zic1+MSX1-1+HES1-1

NeuroD1+MyT1+MSX1-1+HES1-1

NeuroD1+Zic1+MyT1+MSX1-1+HES1-1

The results of these experiments show that Neurofilament M positive transdifferentiated cells also express neural specific tubulin, neural specific enolase, and microtubule associated protein 2. Expression of a number of neuronal antigens and morphological changes (neurites 50 microns or longer) of transdifferentiated cells shows that the procedure of transdifferention results in normal and viable neuronal cells that can be used in cell therapy applications. Moreover, the newly formed neuronal cells of the present invention have the morphological and functional criteria of neurons: they develop long neurites with a growth cones at the end, they express a number of neural specific genes, and they do not continue to proliferate in conditions which induce differentiation, such as, in the presence of all-trans retinoic acid ($10^{-7}$M) and BDNF (20 ng/ml).

Finally, staining of treated epidermal cell cultures with antibodies against glial fibrillary acidic protein shows that small percentage (around 5%) of cells also express GFAP. This is an indication that transdifferentiated cells acquire characteristics of astroglial cells, either directly or indirectly. One possible explanation is that expression of neurogenic genes and blocking expression of inhibitors of neurogenesis results in formation of neuronal progenitor cells that differentiate both neurons and astroglial cells in vitro.

EXAMPLE VII

A Gene Therapy Application for Transdifferentiated Neuronal Cells in Parkinson's Disease Parkinson's Disease results mainly from degeneration of dopamine releasing neurons in the substantia nigra of the brain and the resulting depletion of dopamine neurotransmitter in the striatum. The cause of this degeneration is unknown, but the motor degeneration symptoms of the disease can be alleviated by peripherally administering the dopamine precursor, L-dopa, at the early onset of the disease. As the disease continues to worsen, L-dopa is no longer effective, and currently, no further treatment is available. One promising treatment being developed is to transplant dopamine-rich substantia nigra neurons from fetal brain into the striatum of the brain of the patient. Results obtained from various clinical studies look extremely optimistic, however, it is estimated that up to 10 fetal brains are needed to obtain a sufficient number of cells for one transplant operation. This requirement renders unfeasible the wide application of the transplantation of primary fetal neurons as a therapeutic treatment modality. This problem is resolved, however, by utilizing the transdifferentiated neuronal cells of the present invention for treatment of Parkinson's disease.

It is now widely recognized that transplantation of dopamine producing cells is the most promising therapy of treating severe Parkinson's disease. Stable cell populations or cell lines genetically engineered to produce dopamine is essential to an effective therapy. Since tyrosine hydroxylase (TH) is the key enzyme for dopamine synthesis, cloning this gene in an appropriate expression vector is a first step in the method of treatment. Thus, human TH cDNA will be cloned into eukaryotic expression vector under the control of neuronal specific promoter (for example, neurofilament, neural specific enolase). Expression constructs will be transfected into epidermal basal cells of a patient, using high efficiency transfection protocols (Lipofectamine, Ca-coprecipiotation etc.), followed by selection of the clones which demonstrate stable integration of the expression vector. These clones will be used for transdifferentiation procedures to obtain newly formed neurons that express TH. Thus, human neurons derived from transdifferentiated cells of the present invention will be produced which express the tyrosine hydroxylase (TH) gene. These cells will be transplanted into the patient's striatum or brain. First, the cells will be implanted bilaterally in the caudate nucleus and putamen by using Magnetic Resonance Imaging (MRI)-guided stereotactic techniques. The stereotactic frame will be fixed to the skull after administration of local anesthesia. The caudate nucleus and putamen then will be visualized with MRI. Thereafter, under general anesthesia, ten passes with very thin stereotactic needles will be made bilaterally, 4 mm apart in the caudate and putamen. The rationale for track spacing at approximately 4 mm intervals is important because fetal dopamine neuron processes grow several millimeters, reinnervating the host's striatum. Four trajectories for needle tracks in the caudate and six tracks in the putamen will be calculated to avoid the posterior limb of the internal capsule. The entry points for the putamen and caudate tracks will be at two different sites on the surface of the brain. The tracks to the putamen will be approximately vertical with reference to a coronal plane, while the approach to the caudate will be at an angle of approximately 30 degrees.

EXAMPLE VIII

A Gene Therapy Application for Transdifferentiated Neuronal Cells for the Delivery of Nerve Growth Factors to the Brain The transdifferentiated neuronal cells of the present invention can be transfected with nucleic acids encoding nerve growth (neurotrophic) factors of potential interest. Primary examples of growth factors currently in clinical trials or under full development by various companies are listed below in Table II. So far, tests of the effects of growth factors on the brain and nervous system have been limited to direct peripheral injection of large doses of these factors, which carries a significant risk of side effects, since most growth factors affect many different populations of neurons and non-neural tissues. These problems can be overcome by generating transdifferentiated neuronal cell lines that stably express these growth factors and secrete the growth factors after transplantation.

TABLE II

| NEUROTROPIC FACTORS AND DISEASES | |
|---|---|
| NEUROTROPIC FACTOR | DISEASE |
| Nerve growth factor (NGF) | Alzheimer's Disease |
|  | Diabetic neuropathy |
|  | Taxol neuropathy |
|  | Compressive neuropathy |
|  | AIDS-related neuropathy |
| Brain-derived growth factor (BDNF) | Amyotrophic lateral sclerosis |
| Neurotrophin 3 (NT-3) | Large fiber neuropathy |
| Insulin-like growth factor (IGF) | Amyotrophic lateral sclerosis |
|  | Vincristine neuropathy |
|  | Taxol neuropathy |
| Ciliary neurotrophic factor (CNTF) | Amyotrophic lateral sclerosis |
| Glia-derived neurotrophic factor | Parkinson's Disease |

Local delivery of neurotrophic factors has been suggested as a method to treat several neurological conditions (see Table II). Transdifferentiated epidermal cells from patients own skin represent a vehicle for neurotrophic factor delivery. Human neurotrophic factors cDNAs will be cloned into eukaryotic expression vector under the control of neuronal specific promoter (for example, neurofilament or neural specific enolase). Expression constructs will be transfected into epidermal basal cells using high efficiency transfection protocols (Lipofectamine, Ca-coprecipiotation etc.). This procedure is followed by selection of the clones that demonstrate stable integration of expression vector. These clones will then be used for transdifferentiation procedures to obtain newly formed neurons that express particular neurotrophic factors at significantly high levels. Neuronal cells that express these neurotrophic factors will be transplanted into the patients brain and/or nervous system, as described in Example VII, into locations which are in need of neurotrophic factor delivery.

EXAMPLE IX

A Cell Therapy Application for Transdifferentiated Neuronal Cells as a Treatment for Neurotraumas, Stroke and Neurodegenerative Disease In most neurological diseases, unlike Parkinson's Disease, the underlying cause of symptoms cannot be attributed to a single factor. This condition renders the therapeutic approach of introducing a single gene by gene therapy or single neuronal type replacement by cell therapy ineffective. Rather, replacement of the lost, or diseased, host neuronal cells, or even neuronal networks, by healthy cells and neuronal networks is required. The present invention enables us to develop different types of neurons from a patient's own epidermal basal cells. These newly formed neurons can be cultured separately, or together, to stimulate formation of functional neuronal networks that can be used for replacement therapies. Alternatively, different types of neurons can be transplanted and induced to form functional connections between themselves and host neurons, in situ, in the brain or in the spinal cord. Ability to differentiate de novo, formed neurons into variety of neuronal types in vitro and in vivo makes this approach especially powerful and useful for replacement of complex structures and networks in the nervous system.

As an example for restoring local circuitry in the nervous system is the formation of a functional "pattern generator" in the injured spinal cord. Several data demonstrate that a pattern generator functions in humans, and moreover, that physical therapy can stimulate stepping and use of legs in spinal cord injury patients. (For a review, see Wickelgren, I. 1998. Teaching the spinal cord to walk. Research News. *Science* 279, 319–321. 1998). The pattern generator involves different types of interneurons that connect sensory afferents and motoneurons. Transdifferentiated epidermal basal cells will be treated so as to form all major neuronal cell types that are required for functioning of pattern generator. Here cells will be mixed together wherein natural synapse formation will occur. Since pattern generators are composed of major excitatory (glutamatergic, cholinergic) and inhibitory (glycinergic including Renshaw cells, GABAergic) neurons, first, these neuronal types will be generated by the methods of the present invention described above. Second, excitatory and inhibitory neurons produced in the first step will be grown in co-cultures to stimulate formation of functional connections between the neuron cells. This step will yield aggregates of cells which will be transplanted into the injured spinal cord of a patient. An alternative approach will be to develop different neuronal cell types separately, and mix these before transplantation into the spinal cord. By use of these procedures which permits the transplantation of a large number of different excitatory and inhibitory neurons, a functional set of neuronal connections, capable of supporting local functions of the spinal cord will be developed.

EXAMPLE X

Use of Transdifferentiated Neuronal Cells as a Research Tool in the Search for Novel Growth Factors One of the central principles of modern neurobiology is that each of the major projection neurons, if not all neurons, requires specific signals (trophic factors) to reach their target cells and survive. Neuropathies in many diseases may be caused by, or involve lack of, such growth factors. These growth factors represent the next generation of preventative and therapeutic drugs for nervous system disorders, and hence the enormous capitalization has been invested in the search and development of novel growth factors by the biotechnology industry.

Implicit in the observation that mature neurons can be produced from transdifferentiated neurons is the fact that various growth factors can be tested using these cells to assay for final determination of cell types, maturation, and continued support of cell survival. Most of the growth factors known so far in the nervous system were discovered by their effects on peripheral nerves and these most likely represent a very minor fraction of existing growth factors in the brain.

Search for growth factors from the brain has been difficult mainly because particular neuronal cell types are difficult to isolate from the brain and maintain in defined culture conditions. The use of transdifferentiated epidermal cells overcomes this problem and opens new assays to screen potential growth factors.

The different types of neuronal cells that are created from transdifferentiated epidermal basal cells provides a novel research tool for the discovery and analyses of the effect of new, and also already characterized, growth/neurotrophic factors. Epidermal basal cells will be transdifferentiated into different types of neuronal cells characterized by a particular subtype of neurons. These specific neuronal cells will be used to test, or assay, the effect of potential growth factor sources (tissue homogenates, expression cDNA library products, etc.) on the survival and functional characteristics of cells. For example, cell number will be counted for the analysis of survival of neuronal cells after exposure to growth factors. A wide spectrum of experimental analyses of the functional characteristics of these neurons, known in the art, can be performed to assay the effect of these novel growth factors on the newly created neurons. Experimental techniques, based on an electrophysiological characteristic (patch clamp, different types of intracellular recording, etc.) and molecular biological (gene expression profiles, organization of cytoskeleton, organization of ion channels and receptors etc.) will be used to detect effects of potential growth/neurotrophic factors on particular cell types.

EXAMPLE XI

Use of Transdifferentiated Neuronal Cells as a Research Tool in Drug Screening

As more and more neurotransmitter receptors and signal transducing proteins are being identified from the brain, it is becoming clear that the dogma of one neurotransmitter activating one receptor is an over-simplification. Most receptor complexes in neurons are composed of protein subunits encoded by several genes and each gene synthesizes many different variations of the protein. These variations result in a wide range of possible receptor combinations, and not a single receptor that can interact with a neurotransmitter. Consequently, a range of signal output may be produced by a single neurotransmitter action. The specific signal effected by a neurotransmitter on a neuron, then, depends on which receptor complex is produced by the cell. Thus, cellular diversity must parallel the molecular diversity and constitute a major structural element underlying the complexity of brain function.

Drug discovery by traditional pharmacology had been performed without the knowledge of such complexity using whole brain homogenate and animals. These studies mostly produced analogs of neurotransmitters with broad actions and side effects. The next generation of pharmaceutical drugs aimed at modifying specific brain functions may be obtained by screening potential chemicals against neurons displaying a specific profile of neurotransmitters, receptors complexes, and ion channels.

Epidermal basal cells transdifferentiated into neurons in culture can express several neurotransmitters and receptor complexes. Cell lines derived from these cells can be developed which, when differentiated into mature neurons, would display a unique profile of neurotransmitter receptor complexes. Such neuronal cell lines will be valuable tools for designing and screening potential drugs.

Regardless of whether under a particular set of environmental conditions, in vitro, the inventive transdifferentiated cells express all the biochemical, morphological, and functional characteristics of a given neuronal population in vivo, they provide at least useful simulations of neurons for identifying, screening, or isolating promising new drugs or neural growth factors. Once the potential of a chemical agent is identified by the inventive methods, then, further research can be done to verify its actual effect on particular cell populations of the nervous system and ascertain its clinical usefulness. Thus, the inventive methods of screening a potential chemotherapeutic agent are of benefit in finding and developing the next generation of pharmaceutical drugs narrowly aimed at modifying specific brain functions.

Different types of neuronal cells created from transdifferentiated epidermal basal cells of the present invention will provide novel methodologies to screen potential drugs. For example, using the epidermal basal cells from patients with genetic defects that affect nervous system will make it possible to create various types of neuronal cells which also carry this genetic defect. These cells will be used for screening of drugs which potentially have effect on the diseased neurons. Epidermal basal cells will be transdifferentiated into various types of neuronal cells with characteristics of the desired subtype of neurons. These specific neuronal cells will be used to test, or assay, the effect of potential drugs on the survival and functional characteristics of the cells. Cell number will be counted for the analysis of survival of neuronal cells after exposure to drugs. A wide spectrum of electrophysiological (patch clamp, different types of intracellular recording etc.) and molecular biological (gene expression profiles, organization of cytoskeleton, organization of ion channels and receptors etc.) techniques can be used to detect effects of potential drugs on particular cell types.

In summary, the transdifferentiation nerve cell technology of the present invention offers broad and significant potentials for treating nervous system disorders in both the areas of cell and gene therapy, as well as offering a potential new source of human neurons for research and drug screening.

While the invention can be described in connection with what is presently considered to be the most practical and preferred embodiments, it is to be understood that the invention is not limited to the disclosed embodiments, but on the contrary is intended to cover various modifications and equivalent arrangements included within the spirit and scope of the description of the invention and the appended claims. Thus, it is to be understood that variations in the present invention can be made without departing from the novel aspects of this invention as described in the specification and defined in the claims.

We claim:

1. A method of transdifferentiating an epidermal basal cell into a cell having one or more morphological, physiological and/or immunological features of a neuronal cell, comprising:

(a) culturing an epidermal basal cell from a proliferating epidermal basal cell population derived from a patient's skin;

(b) transfecting said epidermal basal cell, in vitro, with one or more eukaryotic expression vector(s) containing at least one cDNA encoding a human neurogenic transcription factor selected from the group consisting of NeuroD1, NeuroD2, ASH1, Zic1, Zic3, and MyT1, such that at least one of the neurogenic transcription factor(s) is expressed in said cell;

(c) growing the transfected cell in the presence of at least one antisense oligonucleotide comprising a segment of a human MSX1 gene and/or human HES1 gene in an amount sufficient to suppress the expression of functional MSX1 gene product and/or HES1 gene product; and (d) growing said epidermal cell with a retinoid and at least one signal molecule selected from the group consisting of CNTF, sonic hedgehog, sonic hedgehog aminoterminal peptide, and IL-6, whereby the cell is transdifferentiated into a cell having one or more morphological, physiological and/or immunological feature(s) of a neuronal cell.

2. The method of claim 1, wherein the eukaryotic expression vector(s) of the transfection step comprise a CMV promoter sequence operatively linked to a DNA(s) encoding the neurogenic transcription factor selected from the group consisting of NeuroD1, NeuroD2, ASH1, Zic1, Zic3, and MyT1, and wherein the DNA sequence encoding the neurogenic transcription factor is of human origin.

3. A transdifferentiated cell produced by the process of claim 1.

4. A kit for converting, in vitro, epidermal basal cell from a proliferating epidermal basal cell population derived from a patient's skin cells into cells having one or more morphological, physiological and/or immunological feature(s) of a neuronal or astroglial cell, said kit comprising:

(A) one or more eukaryotic expression vector(s) containing cDNA encoding a human neurogenic transcription factor selected from the group consisting of NeuroD1, NeuroD2, ASH1, Zic1, Zic3, and MyT1;

(B) at least one antisense oligonucleotide comprising a segment of the human MSX1 gene, the human HES1 gene; and (C) a retinoid and at least one signal molecule selected from the group consisting of CNTF, sonic hedgehog, and sonic hedgehog aminoterminal peptide.

5. The kit of claim 4, further comprising instructions for using (A), (B), and (C) in transdifferentiating a mammalian subject's epidermal basal cell(s).

6. The transdifferentiated cell of claim 3, wherein the cell further displays the physiological feature of a lack of mitotic activity under cell culture conditions which induce differentiation in neural progenitor cells.

7. The transdifferentiated cell of claim 3, wherein the cell is of human origin.

8. The transdifferentiated cell of claim 3, wherein the transdifferentiated cell has a morphological, physiological, or immunological feature specific to an astroglial or oligodendroglial cell.

9. An in vitro cell culture derived from the transdifferentiated cell of claim 3, comprising a plurality of cells that express one or more morphological, physiological and/or immunological feature(s) of a neuronal cell.

10. The method of claim 1, wherein culturing the proliferating epidermal basal cell from a proliferating epidermal basal cell population derived from a patient's skin cell population comprising one or more epidermal basal cell(s) comprises separating basal cells from keratinocytes using a calcium-free medium.

11. The method of claim 1, wherein said antisense oligonucleotide(s) is modified with one or more thio groups.

12. A transdifferentiated mammalian cell having one or more morphological, physiological and/or immunological feature(s) of an astroglial cell, comprising:
   a cultured epidermal basal cell from a proliferating epidermal basal cell population derived from a patient's skin cell transfected with one or more expression vectors comprising a CMV promoter sequence operatively linked to a DNA(s) encoding a neurogenic transcription factor NeuroD1, NeuroD2, ASH1, Zic1, Zic3, or MyT1, wherein the DNA sequence encoding the neurogenic transcription factor is of human origin, said cell being treated with at least one antisense oligonucleotide comprising a segment of a human MSX1 gene or a human HES1 gene, and wherein said cell was grown in the presence of a retinoid and at least one signal molecule selected from the group consisting of CNTF, IL-6, sonic hedgehog, and sonic hedgehog aminoterminal peptide, thereby transdifferentiating said epidermal basal cell into a cell having one or more morphological, physiological and/or immunological feature(s) of an astroglial cell.

13. A kit for converting, in vitro, epidermal basal cell from a proliferating epidermal basal cell population derived from a patient's skin cells into cells having one or more morphological, physiological and/or immunological feature(s) of a neuronal or astroglial cell, said kit comprising:
   (A) one or more eukaryotic expression vector(s) containing cDNA encoding a human neurogenic transcription factor selected from the group consisting of NeuroD1, NeuroD2, ASH1, Zic1, Zic3, and MyT1;
   (B) at least one antisense oligonucleotide comprising a segment of a human MSX1 gene or a human HES1 gene, or both; and
   (C) a retinoid and at least one signal molecule selected from the group consisting of CNTF, sonic hedgehog, and sonic hedgehog aminoterminal peptide.

14. The kit of claim 13, further comprising instructions for using (A), (B), and (C) in transdifferentiating a mammalian subject's epidermal basal cell(s).

15. The transdifferentiated cell of claim 12, wherein the cell further displays the physiological feature of a lack of mitotic activity under cell culture conditions which induce differentiation in neural progenitor cells.

16. The transdifferentiated cell of claim 12, wherein the cell is of human origin.

17. The transdifferentiated cell of claim 12, wherein the transdifferentiated cell has a morphological, physiological, or immunological feature specific to an astroglial or oligodendroglial cell.

18. An in vitro cell culture derived from the transdifferentiated cell of claim 12, comprising a plurality of cells that express one or more morphological, physiological and/or immunological feature(s) of an astroglial cell.

* * * * *